(12) United States Patent
Komorowski

(10) Patent No.: US 10,959,971 B2
(45) Date of Patent: Mar. 30, 2021

(54) COMPOSITIONS CONTAINING INOSITOL-STABILIZED ARGININE SILICATE COMPLEXES AND INOSITOL FOR IMPROVING COGNITIVE FUNCTION IN VIDEO GAMERS

(71) Applicant: NUTRITION 21, LLC, Purchase, NY (US)

(72) Inventor: James R. Komorowski, Trumbull, CT (US)

(73) Assignee: NUTRITION 21, LLC, Harrison, NY (US)

(*) Notice: Subject to any disclaimer, the term of this patent is extended or adjusted under 35 U.S.C. 154(b) by 0 days.

(21) Appl. No.: 16/670,915

(22) Filed: Oct. 31, 2019

(65) Prior Publication Data

US 2020/0138761 A1 May 7, 2020

Related U.S. Application Data

(60) Provisional application No. 62/755,093, filed on Nov. 2, 2018.

(51) Int. Cl.
*A61K 31/198* (2006.01)
*A61P 25/00* (2006.01)
*A61K 31/045* (2006.01)

(52) U.S. Cl.
CPC .......... *A61K 31/198* (2013.01); *A61K 31/045* (2013.01); *A61P 25/00* (2018.01)

(58) Field of Classification Search
CPC ...... A61K 31/198; A61K 31/045; A61P 25/00
USPC ....................................................... 514/565
See application file for complete search history.

(56) References Cited

U.S. PATENT DOCUMENTS

| | | | |
|---|---|---|---|
| 3,337,403 A | 8/1967 | Zentner | |
| 4,297,349 A | 10/1981 | Barcza | |
| 4,385,052 A | 5/1983 | Zackheim et al. | |
| 4,573,996 A | 3/1986 | Kwiatek et al. | |
| 4,597,961 A | 7/1986 | Etscorn | |
| 4,839,174 A | 6/1989 | Baker et al. | |
| 4,847,082 A * | 7/1989 | Sabin .................... | A61K 31/66 514/103 |
| 4,908,213 A | 3/1990 | Govil et al. | |
| 4,943,435 A | 7/1990 | Baker et al. | |
| 5,217,997 A | 6/1993 | Levere et al. | |
| 5,250,569 A | 10/1993 | Godfrey | |
| 5,284,657 A | 2/1994 | Lu et al. | |
| 5,288,497 A | 2/1994 | Stanley et al. | |
| 5,622,980 A | 4/1997 | Caldwell et al. | |
| 5,656,264 A | 8/1997 | Hanada et al. | |
| 5,662,920 A | 9/1997 | Santus | |
| 5,707,970 A | 1/1998 | McCarty et al. | |
| 5,716,610 A | 2/1998 | Jack et al. | |
| 5,763,392 A | 6/1998 | Hansen et al. | |
| 5,763,496 A | 6/1998 | Holland | |
| 5,804,203 A | 9/1998 | Hahn et al. | |
| 6,066,659 A | 5/2000 | Speck | |
| 6,123,936 A | 9/2000 | Platz et al. | |
| 6,132,394 A | 10/2000 | Lankinen | |
| 6,156,735 A | 12/2000 | McCarty et al. | |
| 6,182,655 B1 | 2/2001 | Keller et al. | |
| 6,298,847 B1 | 10/2001 | Datta et al. | |
| 6,344,444 B1 | 2/2002 | McCarty et al. | |
| 6,387,394 B1 | 5/2002 | Baichwal et al. | |
| 6,418,926 B1 | 7/2002 | Chawla | |
| 6,462,051 B1 | 10/2002 | Nozawa et al. | |
| 6,803,456 B1 | 10/2004 | Kuhlmann | |
| 7,576,132 B2 | 8/2009 | Juturu et al. | |
| 2002/0068365 A1 | 6/2002 | Kuhrts | |
| 2003/0028169 A1 | 2/2003 | Fossel | |
| 2004/0009746 A1 | 1/2004 | Korman | |
| 2004/0097472 A1 | 5/2004 | Juturu et al. | |
| 2004/0204387 A1 | 10/2004 | McLaurin | |
| 2006/0204455 A1 | 9/2006 | Giniger | |
| 2007/0116831 A1 | 5/2007 | Prakash et al. | |
| 2012/0141588 A1 | 6/2012 | Chopra et al. | |
| 2016/0081959 A1 | 3/2016 | Bartos et al. | |
| 2016/0263135 A1 | 9/2016 | Komorowski et al. | |
| 2017/0000809 A1 | 1/2017 | Komorowski | |
| 2017/0135969 A1 | 5/2017 | Komorowski | |

FOREIGN PATENT DOCUMENTS

| | | |
|---|---|---|
| EP | 2805730 | 11/2014 |
| FR | 2610522 | 8/1989 |
| FR | 2745498 | 9/1997 |
| WO | WO-98/34647 | 8/1998 |
| WO | WO-00/45651 | 8/2000 |
| WO | WO-02/28379 | 4/2002 |
| WO | WO-2004/017913 | 3/2004 |
| WO | WO-2012/173808 | 12/2012 |

(Continued)

OTHER PUBLICATIONS

U.S. Appl. No. 60/405,749, filed Aug. 22, 2002, Juturu et al.
U.S. Appl. No. 62/187,120, filed Jun. 30, 2015, Komorowski.
U.S. Appl. No. 62/948,591, filed Dec. 16, 2019, Komorowski.
Ansel's Pharmaceutical Dosage Forms and Drug Delivery Systems, 8th Edition, Allen et al. eds., Lippincott Williams & Wilkins, Philadelphia, PA, 2005.
Asai et al., "Topical application of ex vivo expanded endothelial progenitor cells promotes vascularization and wound healing in diabetic mice," International Wound Journal, 2012: pp. 527-533.
Ask the dentist, how often should I go to the dentist for a teeth cleaning? [online], [retrieved Jul. 21, 2018]. Retrieved from the Internet: <URL: https://askthedentist.com/how-often-should-i-go-to-the-dentist-for-a-teeth-cleaning/>.

(Continued)

*Primary Examiner* — Kevin E Weddington
(74) *Attorney, Agent, or Firm* — Arnall Golden Gregory LLP

(57) ABSTRACT

The present disclosure relates to the use of inositol-stabilized arginine silicate complexes ("ASI") with the addition of free inositol ("I") to form a composition ASI+I for improving cognitive functioning in humans, particularly video game players.

10 Claims, 2 Drawing Sheets

(56) References Cited

FOREIGN PATENT DOCUMENTS

| WO | WO-2017/004226 | 1/2017 | | |
|---|---|---|---|---|
| WO | WO-2017004226 A1 | * | 1/2017 | ........... A61K 31/198 |

OTHER PUBLICATIONS

Bassler, "Hard water, food fibre, and silicon," British Medical Journal, 1978; 1: p. 919.
Bonnefont-Rousselot, "Glucose and reactive oxygen species," Curr. Opin. Clin. Nutr. Metab. Care, 2002; 5: pp. 561-568.
Calles-Escandon et al., "Diabetes and endothelial dysfunction: A clinical perspective." Endocrine Reviews, 2001; 22(1): pp. 36-52.
Calver et al., "Effect of local intra-arterial NG -monomethyl-L-arginine in patients with hypertension: the nitric oxide dilator mechanism appears abnormal," J. of Hypertension, 1992; 10: pp. 1025-1031.
Carlisle et al., "A silicon requirement for normal growth of cartilage in culture," Fed. Proc., 1980; 39: p. 787.
Carlisle, "Biochemical and morphological change associated with long bone abnormalities in silicon deficiency," J. Nutr., 1980; 110: pp. 1046-1055.
Carlisle, "In vivo Requirement for Silicon in Articular Cartilage and Connective Tissue Formation in the Chick," J. Nutr., 1976; 106: pp. 478-484.
Carlisle, "Silicon: An Essential Element for the Chick," Science, 1972; 178: pp. 619-621.
Chen et al., "L-Arginine Abrogates Salt-sensitive Hypertension in Dah/Rapp Rats," J. Clin. Invest., 1991; 88: pp. 1559-1567.
Cherian et al., "L-arginine and Free Radical Scavengers Increase Cerebral Blood Flow and Brain Tissue Nitric Oxide Concentrations after Controlled Cortical Impact Injury in Rats," J. of Neurotrauma, 2003; 20(1): pp. 77-85.
Clarkson et al., "Oral L-Arginine Improves Endothelium-dependent Dilation in Hypercholesterolemic Young Adults," J. Clin. Invest., 1996; 97(8): pp. 1989-1994.
Clowes et al., "Suppression by heparin of smooth muscle cell proliferation in injured arteries," Nature, 1977; 265: pp. 625-626.
Cooke et al., "Is NO An Endogenous Antiatherogenic Molecule," Arteriosclerosis and Thrombosis, 1994; 14(5): pp. 653-655.
Cosgrove, "Nitric Oxide Ingredients for Sports," Nutritional Outlook, [online], Nov. 8, 2013. Retrieved from the Internet: <URL: http://www.nutritionaloutlook.com/heart-health/nitric-oxide-ingredients-sports>.
Creager et al., "L-Arginine Improves Endothelium-dependent Vasodilation in Hypercholesterolemic Humans," J. Clin. Invest., 1992; 90: pp. 1248-1253.
Curtis et al., "Nitric oxide supplementation or synthesis block-which is the better approach to treatment of heart disease?," Trends in Pharmacological Sciences, 1997; 18(7): pp. 239-244.
Drexler et al., "Correction of endothelial dysfunction in coronary microcirculation of hypercholesterolaemic patients by L-arginine," Lancet, 1991; 338: pp. 1546-1550.
Edelman et al., "Effect of controlled adventitial heparin delivery on smooth muscle cell proliferation following endothelial injury," Proc. Natl. Acad. Sci. USA, 1990; 87: pp. 3773-3777.
Eisinger et al., "Effects of silicon, fluoride, etidronate and magnesium on bone mineral density: a retrospective study," Magnisium Research, 1993; 6(3): pp. 247-249.
Garson et al., "Organosilicon Entities as Prophylactic and Therapeutic Agents," J. of Pharmaceutical Sciences, 1971; 60(8): pp. 1113-1127.
Geoffrey Stark, DDS, How much toothpaste per brushing is recommended? [online], [retrieved Jul. 23, 2018]. Retrieved from the Internet: <URL: https://secure.advantagedental.com/images/files/faq_toothpaste.htm>.
Goodman and Gilman's: The Pharmacological Basis of Therapeutics, 8th Ed., Gilman et al., eds., Pergamon Press, Elmsford, NY, 1990.

Greenhalgh et al., "PDGF and FGF stimulate wound healing in the genetically diabetic mouse," American Journal of Pathology, 1990; 136(6):1235-1246.
Guyton et al., "Inhibition of rat arterial smooth muscle cell proliferation by heparin," Circ. Res., 1980; 46: pp. 625-634.
Harrison's Principles of Internal Medicine, 13th edition, vol. 2, Isselbacher et al. (eds.), published 1994 by McGraw-Hill in 1994, p. 1321.
Hott et al., "Short-term effects of organic silicon on trabecular bone in mature ovariectomized rats," Calcif. Tissue Int., 1993; 53: pp. 174-179.
International Search Report and Written Opinion dated Aug. 26, 2016 in PCT/US16/040128.
International Search Report and Written Opinion dated Jan. 27, 2020 in PCT/US19/58653.
Kelly et al., "Insulin resistance: lifestyle and nutritional interventions," Alternative Medicine Review, 2000; 5(2): pp. 109-132.
Kelly et al., "L-Theanine and Caffeine in Combination Affect Human Cognition as Evidenced by Oscillatory alpha-Band Activity and Attention Task Performance," J. Nutr., 2008; 138(8): pp. 1572S-1577S.
Kottke et al., Chapter 10: Tablet Dosage Forms, in Modern Pharmaceutics, 4th Edition, Banker et al., eds., Marcel Dekker, Inc., New York NY, 2002: pp. 287-333.
Laurant et al., "Dietary L-Arginine Attenuates Blood Pressure in Mineralocorticoid-Salt Hypertensive Rats," Clin. And Exper. Hypertension, 1995; 17(7): pp. 1009-1024.
Im-Emsap et al., Chapter 9: Disperse Systems, in Modern Pharmaceutics, 4th Edition, Banker et al., eds., Marcel Dekker, Inc., New York NY, 2002: pp. 237-285.
Loeper et al., "The Antiatheromatous Action of Silicon," Atherosclerosis, 1979; 33: pp. 397-408.
Loeper et al., "The Physiological Role of the Silicon and its Antiatheromatous Action, in Biochemistry of Silicon and Related Problems," Bendz G. et al. Eds..Plenum Press, NY, 1978; pp. 281-296.
Luscher, "Endothelium-derived nitric oxide: The endogenous nitrovasodilator in the human cardiovascular system," Eur. Heart J., 1991; 12(Suppl. E): pp. 2-11.
Marsh et al., "Relationships Among Balance, Visual Search, and Lacrosse-Shot Accuracy," J Strength Cond Res, 2010; 24(6): pp. 1507-1514.
Maulik et al., "Nitric Oxide signaling in ischemic heart," Cardiovasc. Res., 1995; 30(4): pp. 593-601.
McPherson et al., "Superoxide activates constitutive nitric oxide synthase in a brain particulate fraction," Biochemical and Biophysical Research Communications, 2002; 296: pp. 413-418.
Miller et al., "Practical Clinical Application of Biochemical Markers of Bone Turnover," Journal of Clinical Densitometry, 1999; 2(3): pp. 323-342.
Mind Lab Pro®, "Nootropics for Ganiers—Level Up Your Ganiing \Nith Cognitive Enhancers," Nootropics for Gamers—Level Up Your Gaming with Cognitive Enhancers, 2018, [online], [retrieved on Dec. 18, 2019]. Retrieved from the Internet: <URL: https://www.mindlabpro.com/blogs/nootropics/nootropics-gamers-gaming>.
Moncada et al., "The L-Arginine-Nitric Oxxide Pathway," The New. Engl. J. of Med., 1993; 329(27): pp. 2002-2012.
Nutrition 21, Inc., EurekAlert!, [online], public release Dec. 13, 2007. Retrieved from the Internet: <URL: https://www.eurekalert.org/pub_releases/2007-12/n2-ncd121207.php>.
Parr, "Silicon, Wine, and the Heart," Lancet, 1980; p. 1087.
Partial European Search Report for European Application No. 03793307.4, dated Aug. 2, 2007.
Pharmaceutical Dosage Forms: Tablets, Lieberman et al., eds., Marcel Dekker, Inc., New York, NY, 1989.
Proctor et al., "Metabolic effects of a novel silicate inositol complex of the nitric oxide precursor arginine in the obese insulin-resistant JCR:LA-cp rat," Metabolism Clinical and Experimental, 2007; 56: pp. 1318-1325.
Proctor et al., "A novel complex of arginine-silicate improved micro and macrovascular function and inhibits glomerular sclerosis in insulin-resistant JCR:LA-cp rats," Diabetologia, 2005; 48(9): pp. 1925-1932.

(56) References Cited

OTHER PUBLICATIONS

Rood-Ojalvo et al., "The benefits of inositol-stabilized arginine silicate as a workout Ingredient," Journal of the International Society of Sports Nutrition, 2015; 12(suppl. 1): p. 14.

Rubanyi, "Endothelium-Derived Vasoactive Factors in Health and Disease, in Cardiovascular Significance of Endothelium-Derived Vasoactive Factors," Rubanyi, G.M., ed., Futura Publishing Company, Inc., NY xi-xix, 1991.

Salt metathesis reaction, Wikipedia [online], [retrieved 2018]. Retrieved from the Internet: <URL: https://en.wikipedia.org/wiki/Salt_metathesis_reaction>.

Saul, [online], [retrieved on Nov. 27, 2017]. Retrieved from the Internet: <URL: <http://www.doctoryourself.com/fatigue.html>, 2005.

Schiffman et al., "Taste of nutrients: amino acids, vitamins and fatty acids," Perception & Physcophisics, 1975; 17(2): pp. 140-146.

Schwarz et al., "Growth-promoting Effects of Silicon in Rats," Nature, 1972; 239: pp. 333-334.

Schwarz et al., "Inverse Relation of Silicon in Drinking Water and Atherosclerosis in Finland," Lancet, 1977; pp. 538-539.

Schwarz, "Significance and Functions of Silicon in Warm-Blooded Animals, in Biochemistry of Silicon and Related Problems," Bendz, G. et al., Eds., Plenum Press, NY 207-230 (1978).

Schwarz, "Silicon, Fibre, and Atherosclerosis," Lancet, 1977; pp. 454-457.

Supplementary European Search Report for European Application No. EP 03793307.4 dated Dec. 4, 2008.

Svehla, "Reaction of Silicates," Vogels Textbook of Macro and Semimicro Qualitative Inorganic Analysis 5th Edition, Longman, London, 1979; pp. 350-353.

Toker et al., "The effects of hydrogen sulphide on alveolar bone loss in periodontitis," Minerva Stomatol, 2014; 63(4): pp. 103-110.

Tsao et al., "Enhanced endothelial adhesiveness in hypercholesterolemia is attenuated by L-arginine," Circulation, 1994; 89(5): pp. 2176-2182.

Van Lente, "Markers of inflammation as predictors in cardiovascular disease," Clinica Chimica Acta., 2000; 293: pp. 31-52.

Wang et al. "Effects of nitric oxide synthase inhibitors on systemic hypotension, cytokines and inducible nitric oxide synthase expression and lung injury following indotoxin administration in rats," J. Biomed. Sci., 1999; 6: pp. 28-35.

Nitric Oxide Benefits, Supplements, Sources, and Side Effects, [online], [dated May 24, 2015]. Retrieved from the Internet: <URL: https://web.archive.org/web/20150524100645/http://www.nitricoxide.org: 80/>.

Nitrosigine Launch, [online], [dated May 16, 2013]. Retrieved from the Internet: <URL: https://nutrition21.com/nutrition-21-launches-nitrosigine-a-novel-patented-source-of-inositol-stabilized-arginine-silicate-accepted-by-the-fda-as-a-new-dietary-ingredient/>.

Wilson et al., "Impaired cognitive function and mental performance in mild dehydration," European Journal of Clinical Nutrition, 2003; 57(2): pp. S24-S29.

* cited by examiner

COMPOSITIONS CONTAINING INOSITOL-STABILIZED ARGININE SILICATE COMPLEXES AND INOSITOL FOR IMPROVING COGNITIVE FUNCTION IN VIDEO GAMERS

CROSS-REFERENCE TO RELATED APPLICATIONS

This application claims priority to of U.S. Provisional Application No. 62/755,093 filed Nov. 2, 2018, the contents of which is incorporated by reference herein in its entirety.

BACKGROUND

The present disclosure relates to new uses of an inositol-stabilized arginine silicate complex. Such complexes are commercially available and sold as, for example, Nitrosigine®. Nitrosigine® has been clinically shown to boost nitric oxide ("NO") levels. Nitric oxide is a key factor in promoting the relaxation of smooth muscle in blood vessels, increasing blood flow to working muscles. In general, the complex is produced by combining arginine, a silicate salt and inositol. Although the compositions described herein generally contain arginine, silicate and inositol, it may be referred to throughout the specification as "inositol-stabilized arginine silicate," "arginine silicate," "arginine silicate inositol," "ASI," "Nitrosigine®," or "complex."

Disclosed herein is the surprising result that ASI, when combined with free inositol can improve a subject's cognitive function. Accordingly, compositions containing ASI and free inositol may be used to improve cognitive functioning in humans. Improved cognitive functioning may be particularly desirable when a subject is fatigued. Fatigue may result from, for example, a lack of sleep and/or after periods of increased mental and/or physical activity. The compositions of the present invention may be administered to subjects and may enhance mental focus and/or mental clarity in the subjects. The compositions of the present invention may be particularly helpful for use in improving the performance of people required to perform complex tasks when rested and/or fatigued, such as video gamers, athletes, operators of unmanned vehicles and remote controlled vehicles and the like.

SUMMARY

Some embodiments include the use of compositions containing ASI and free inositol for improving cognition. Some embodiments include administering an amount of compositions containing ASI and free inositol effective to improve cognition in humans. Some embodiments include the use of compositions containing ASI and free inositol for improving mental focus and/or attention span.

Some embodiments include the use of compositions containing ASI and free inositol for improving the performance of complex tasks performed by humans. Such improvement may be in the form of a reduced number of errors in performance of the complex task in comparison to a baseline. Some embodiments include administration of a composition comprising an effective amount of ASI and free inositol. The compositions may be formulated for oral delivery. The compositions may be self-administered.

Figure 1:
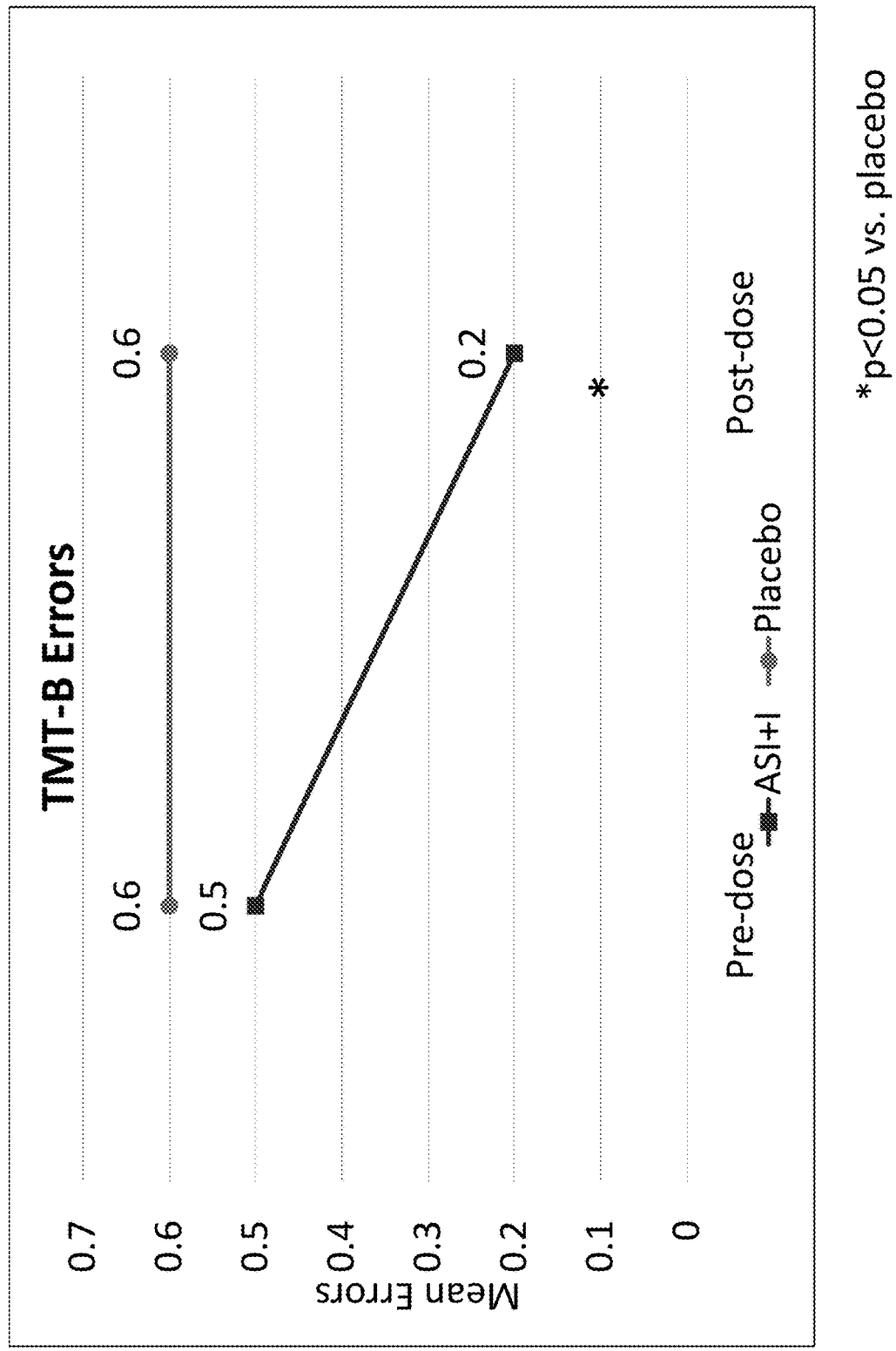
FIG. 1 is a line graph summarizing the results of average number of errors committed by subjects in trail making test B. Subjects received either placebo or a composition comprising ASI (1,500 mg) and free inositol (100 mg). Trail making test B was performed prior to treatment (baseline) and 15 minutes post-administration of the composition.

While the present invention has been described in some detail for purposes of clarity and understanding, one skilled in the art will appreciate that various changes in form and detail can be made without departing from the true scope of the invention.

DETAILED DESCRIPTION

The terminology used in the description presented herein is not intended to be interpreted in any limited or restrictive manner, simply because it is being utilized in conjunction with a detailed description of certain specific embodiments described herein. Furthermore, embodiments described herein can include several novel features, no single one of which is solely responsible for its desirable attributes or which is essential to practicing the embodiments described herein.

As used in the claims below and throughout this disclosure, the phrase "consisting essentially of" is meant including any elements listed after the phrase, and limited to other elements that do not interfere with or contribute to the activity or action specified in the disclosure for the listed elements. Thus, the phrase "consisting essentially of" indicates that the listed elements are required or mandatory, but that other elements are optional and can or cannot be present depending upon whether or not they affect the activity or action of the listed elements. For example, the use of a composition "consisting essentially of ASI" for the treatment of a particular disease or disorder would exclude other ingredients that were known to be active in combating the particular disease or disorder.

A "therapeutically effective amount" or "effective amount" as used herein includes within its meaning a non-toxic but sufficient amount of a compound active ingredient or composition comprising the same for use in the embodiments disclosed herein to provide the desired therapeutic effect. Similarly "an amount effective to" as used herein includes within its meaning a non-toxic but sufficient amount of a compound active ingredient or composition comprising the same to provide the desired effect. The exact amount of the active ingredient disclosed herein required will vary from subject to subject depending on factors such as the species being treated, the age and general condition of the subject, the severity of the condition being treated, the particular agent being administered, the weight of the subject, and the mode of administration and so forth. Thus, it is not possible to specify an exact "effective amount." However, for any given case, an appropriate "effective amount" may be determined by one of ordinary skill in the art using only routine methods. In some aspects, a therapeutically effective amount may include a dosing regimen. For example, an effective amount may include about 1,500 mg of ASI and 100 mg of free inositol orally consumed each day for three consecutive days. In some aspects, a therapeutically effective amount may include about 1,500 mg of ASI and 100 mg of free inositol orally consumed each day for fourteen consecutive days. Compositions of the present invention may include, for example, between 0.01-5 grams of ASI and 0.01-1 grams of free inositol.

By way of example, a "therapeutically effective amount" of the composition disclosed herein can be, for example, 0.1 µg/kg, 0.5 µg/kg, 1 µg/kg, 1.5 µg/kg, 2.0 µg/kg, 2.5 µg/kg, 3.0 µg/kg, 3.5 µg/kg, 4.0 µg/kg, 4.5 µg/kg, 5.0 µg/kg, 10 µg/kg, 15 µg/kg, 20 µg/kg, 25 µg/kg, 30 µg/kg, 35 µg/kg, 40 µg/kg, 45 µg/kg, 50 µg/kg, 55 µg/kg, 60 µg/kg, 65 µg/kg, 70 µg/kg, 75 µg/kg, 80 µg/kg, 85 µg/kg, 90 µg/kg, 95 µg/kg, 100 µg/kg, 150 µg/kg, 200 µg/kg, 250 µg/kg, 300 µg/kg, 350 µg/kg, 400 µg/kg, 450 µg/kg, 500 µg/kg, 550 µg/kg, 600 µg/kg, 650 µg/kg, 700 µg/kg, 750 µg/kg, 80 µg/kg 0, 850 µg/kg, 900 µg/kg, 1 mg/kg, 1.5 mg·kg, 2.0 mg/kg, 2.5 mg/kg, 3 mg/kg, 4.0 mg/kg, 5.0 mg/kg, 6 mg/kg, 7 mg/kg, 8 mg/kg, 9 mg/kg, 10 mg/kg, 15 mg/kg, 20 mg/kg, 25 mg/kg, 30 mg/kg, 35 mg/kg, 40 mg/kg, 45 mg/kg 50 mg/kg, 55 mg/kg, 60 mg/kg, 65 mg/kg, 70 mg/kg, 75 mg/kg, 80 mg/kg, 85 mg/kg, 90 mg/kg, 95 mg/kg, 100 mg/kg, 125 mg/kg, 150 mg/kg, 200 mg/kg, 250 mg/kg, 300 mg/kg, 350 mg/kg, 400 mg/kg, 450 mg/kg, 500 mg/kg, 550 mg/kg, 600 mg/kg, 650 mg/kg, 700 mg/kg, 750 mg/kg, 800 mg/kg, 850 mg/kg, 900 mg/kg, 950 mg/kg, 1 g/kg, 5 g/kg, 10 g/kg, or more, or any fraction in between of the ASI complex and the free inositol.

Accordingly, in some embodiments, the dose of the compositions disclosed herein can be about 100 µg to about 100 g, preferably per day. For example, the amount of the composition can be 100 µg, 125 µg, 150 µg, 175 µg, 200 µg, 225 µg, 250 µg, 275 µg, 300 µg, 325 µg, 350 µg, 375 µg, 400 µg, 425 µg, 450 µg, 475 µg, 500 µg, 525 µg, 575 µg, 600 µg, 625 µg, 650 µg, 675 µg, 700 µg, 725 µg, 750 µg, 775 µg, 800 µg, 825 µg, 850 µg, 875 µg, 900 µg, 925 µg, 950 µg, 975 µg, 1000 µg, 1.25 g, 1.5 g, 1.75 g, 2.0 g, 2.25 g, 2.5 g, 2.75 g, 3.0 g, 3.25 g, 3.5 g, 3.5 g, 3.75 g, 4.0 g, 4.25 g, 4.5 g, 4.75 g, 5.0 g, 5.25 g, 5.5 g, 5.75 g, 6.0 g, 6.25 g, 6.5 g, 6.75 g, 7.0 g, 7.25 g, 7.5 g, 7.75 g, 8.0 g, 8.25 g, 8.5 g, 8.75 g, 9.0 g, 8.25 g, 9.5 g, 9.75 g, 10 g, 20 g, 30 g, 40 g, 50 g, 60 g, 70 g, 80 g, 90 g, 100 g, or more, or any range or amount in between any two of the preceding values. The exemplary therapeutically effective amounts listed above, can, in some embodiments be administered in the methods described elsewhere herein on an hourly basis, e.g., every one, two, three, four, five, six, seven, eight, nine, ten, eleven, twelve, thirteen, fourteen, fifteen, sixteen, seventeen, eighteen, nineteen, twenty, twenty-one, twenty-two, twenty-three hours, or any interval in between, or on a daily basis, every two days, every three days, every four days, every five days, every six days, every week, every eight days, every nine days, every ten days, every two weeks, every month, or more or less frequently, as needed to achieve the desired effect.

Advantageously, an effective amount may be between about 20 mg and about 5,000 mg per day of the ASI and between about 10 mg and 1000 mg per day of the free inositol. More advantageously, the effective amount is between about 500 mg and about 2,000 mg per day of the ASI and between about 50 mg and 500 mg per day of the free inositol. Effective doses may be extrapolated from dose-response curves derived from in vitro or animal model test systems. Such animal models and systems are well known in the art.

The term "free inositol" means inositol that is separate from and not bound to, or otherwise associated with, or combined in, an inositol-stabilized arginine silicate complex, or any other compound. As described above, an inositol-stabilized arginine silicate complex is produced by combining arginine, a silicate salt and inositol. The term "free inositol" does not include inositol used in the production of the inositol-stabilized arginine silicate complex.

The term "unmanned vehicle" means any type of vehicle that does not carry any human and which is controlled remotely by a human via a remote computer or device and a means for communicating between the vehicle and the remote computer or device, such as an internet connection, a Bluetooth connection, a wireless connection, a satellite connection, and the like. Examples of "unmanned vehicles" include, but are not limited to, drones, missiles, spacecraft and the like. The term "remote controlled vehicle" means any type of vehicle that may carry any human, and which is controlled remotely by a human via a remote computer or device and a means for communicating between the vehicle and the remote computer or device, such as an internet connection, a Bluetooth connection, a wireless connection, a satellite connection, and the like. Examples of "remote controlled vehicles" include, but are not limited to, driverless cars, driverless trains, driverless buses, pilotless airplanes, and the like.

The present application is directed, in part, to the surprising discovery that inositol-stabilized arginine silicate complexes with additional free inositol improve cognitive function. Described herein are various dosing amounts, schedules, formulations, and delivery systems for inositol-stabilized arginine silicate complexes with additional free inositol for use in the improvement of cognitive function, and/or the increasing of cognitive function.

Some embodiments provide methods of improving cognitive function in an individual. In some embodiments, improving cognitive function comprises improving visual construction in an individual. In some embodiments, improving cognitive function comprises improving executive function in an individual. In some embodiments, improving cognitive function comprises improving visual search in an individual. In some embodiments, improving cognitive function comprises improving motor speed skills in an individual. In some embodiments, improving cognitive function comprises improving mental flexibility in an individual. In some embodiments, improving cognitive function comprises improving selective attention in an individual. In some embodiments, improving cognitive function comprises improving interference resolution in an individual. In some embodiments, improving cognitive function comprises improving response inhibition in an individual. In some embodiments, improving cognitive function comprises improving response selection in an individual. In some embodiments, improving cognitive function comprises improving reaction time in an individual.

In some embodiments, improving cognition comprises improving the speed (i.e., decreasing the time) for a Trail Making Test. In some embodiments, improving cognition comprises decreasing the number of errors in a Trail Making Test. In some embodiments, improving cognition comprises both increasing the speed and decreasing the number of errors in a Trail Making Test. In some embodiments, improving cognition comprises improving the speed (i.e., decreasing the time) for a Stroop Test. In some embodiments, improving cognition comprises decreasing the number of errors in a Stroop Test. In some embodiments, improving cognition comprises both increasing the speed and decreasing the number of errors in a Stroop Test. In some embodiments, improving cognition comprises improving performance when playing a video game. In some embodiments, improving performance when playing a video game comprises increasing a high score in a video game, playing the game at a more difficult level/setting, scoring more points/goals in a sports simulation video game, hitting more targets in a shooter video game, beating more opponents in a multiplayer video game, and/or hitting an opponent more times in a fight simulation video game and the like. In some embodiments, improving cognition comprises more accurate control of an unmanned vehicle. In some embodiments, more accurate control of an unmanned vehicle comprises decreasing the number errors while controlling the unmanned vehicle. In some embodiments, more accurate control of an unmanned vehicle comprises increasing the number of targets acquired by the unmanned vehicle. In some embodiments, more accurate control of remote controlled vehicle comprises decreasing the number errors while controlling the remote controlled vehicle.

In some embodiments, the cognitive improvement is observed after about 15 minutes; after about 60 minutes; after about 1 day; after about 3 days; one week; after about two weeks; after about three weeks; after about four weeks; after about six weeks; after about eight weeks; after about 3 months; after about 4 months; after about 6 months; after about 9 months; after about 12 months; after about 18 months; or after about 24 months.

Enhanced mental flexibility has been shown to benefit athletes when faced with quick decisions and associated adaptations often required during competition, especially in field sports such as football. In addition, the ability to efficiently allocate attention is an important factor for success in all sports. The ability to multitask may help an athlete save energy through more efficient processing, thus also allowing them to perform better than they had previously. Skilled athletes who adapt to rapid changes in visual information are able to allocate their attention more effectively than less skilled athletes. They are then able to use visual scanning techniques as well as speed and anticipation to make changes in their performance. This enhanced mental flexibility allows the athlete to adjust his or her "game" faster than their peers.

Furthermore, a study of female collegiate lacrosse players demonstrated that TMT B scores were positively related to less lacrosse-shot error or less unsuccessful shots. Marsh, D. W., Richard, L. A., Verre, A. B., Myers, J. (2010), *Relationships Among Balance, Visual Search, and Lacrosse-Shot Accuracy*, J of Str & Cond Res, 24(6):1507-1514. This suggests that successful sports performance encompasses a complex interaction of physical and cognitive skills and that perhaps even a small improvement can make an impact on performance.

The administration of the compositions disclosed herein can be by any of the methods of administration described herein or by delivery methods known by one of skill in the art. The compositions may be administered orally.

For oral administration, the compositions disclosed herein can be provided as a tablet, aqueous or oil suspension, dispersible powder or granule, emulsion, hard or soft capsule, syrup, elixir, or beverage. Compositions intended for oral use can be prepared according to any method known in the art for the manufacture of pharmaceutically acceptable compositions and such compositions may contain one or more of the following agents: sweeteners, flavoring agents, coloring agents and preservatives. The sweetening and flavoring agents will increase the palatability of the preparation. Tablets containing the composition of the present invention in admixture with non-toxic pharmaceutically acceptable excipients suitable for tablet manufacture are acceptable. Pharmaceutically acceptable vehicles such as excipients are compatible with the other ingredients of the formulation (as well as non-injurious to the patient). Such excipients include inert diluents such as calcium carbonate, sodium carbonate, lactose, calcium phosphate or sodium phosphate; granulating and disintegrating agents, such as corn starch or alginic acid; binding agents such as starch, gelatin or acacia; and lubricating agents such as magnesium stearate, stearic acid or talc. Tablets can be uncoated or can be coated by known techniques to delay disintegration and absorption in the gastrointestinal tract and thereby provide a sustained action over a longer period of time. For example, a time delay material such as glyceryl monostearate or glyceryl distearate alone or with a wax can be employed.

Formulations for oral use can also be presented as hard gelatin capsules wherein the compositions of the present invention are mixed with an inert solid diluent, for example calcium carbonate, calcium phosphate or kaolin, or as soft gelatin capsules wherein the active ingredient is mixed with water or an oil medium, such as peanut oil, liquid paraffin or olive oil. Aqueous suspensions can contain the compositions of the present invention in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

Oil suspensions can be formulated by suspending the compositions of the present invention in a vegetable oil, such as *arachis* oil, olive oil, sesame oil or coconut oil, or in a mineral oil such as liquid paraffin. The oil suspension can contain a thickening agent, such as beeswax, hard paraffin or cetyl alcohol. Sweetening agents, such as those set forth above, and flavoring agents can be added to provide a palatable oral preparation. These compositions can be preserved by an added antioxidant such as ascorbic acid. Dispersible powders and granules of the invention suitable for preparation of an aqueous suspension by the addition of water provide the compositions of the present invention in admixture with a dispersing or wetting agent, a suspending agent, and one or more preservatives. Additional excipients, for example sweetening, flavoring and coloring agents, can also be present.

Syrups and elixirs can be formulated with sweetening agents, such as glycerol, sorbitol or sucrose. Such formulations can also contain a demulcent, a preservative, a flavoring or a coloring agent.

The compositions can also be in the form of oil-in-water emulsions. The oily phase can be a vegetable oil, such as olive oil or arachis oil, a mineral oil such as liquid paraffin, or a mixture thereof. Suitable emulsifying agents include naturally-occurring gums such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsions can also contain sweetening and flavoring agents.

Aqueous suspensions may contain the compositions of the present invention disclosed herein in admixture with excipients suitable for the manufacture of aqueous suspensions. Such excipients include suspending agents, dispersing or wetting agents, one or more preservatives, one or more coloring agents, one or more flavoring agents and one or more sweetening agents such as sucrose or saccharin.

The disclosed compositions of the present invention can also be administered by inhalation. In this administration route, compositions of the present invention can be dissolved in water or some other pharmaceutically acceptable carrier liquid for inhalation, or provided as a dry powder, and then introduced into a gas or powder that is then inhaled by the patient in an appropriate volume so as to provide that patient with a measured amount of compositions of the present invention.

Controlled release vehicles are well known to those of skill in the pharmaceutical sciences. The technology and products in this art are variably referred to as controlled release, sustained release, prolonged action, depot, repository, delayed action, retarded release and timed release; the words "controlled release" as used herein is intended to incorporate each of the foregoing technologies.

Numerous controlled release vehicles are known, including biodegradable or bioerodible polymers such as polylactic acid, polyglycolic acid, and regenerated collagen. Known controlled release drug delivery devices include creams, lotions, tablets, capsules, gels, microspheres, liposomes, ocular inserts, minipumps, and other infusion devices such as pumps and syringes. Implantable or injectable polymer matrices, and transdermal formulations, from which active ingredients are slowly released, are also well known and can be used in the disclosed methods.

Controlled release preparations can be achieved by the use of polymers to form complexes with or absorb the compositions of the present invention. The controlled delivery can be exercised by selecting appropriate macromolecules such as polyesters, polyamino acids, polyvinylpyrrolidone, ethylenevinyl acetate, methylcellulose, carboxymethylcellulose, and protamine sulfate, and the concentration of these macromolecule as well as the methods of incorporation are selected in order to control release of compositions of the present invention.

Controlled release of active complexes can be taken to mean any of the extended release dosage forms. The following terms may be considered to be substantially equivalent to controlled release, for the purposes of the present disclosure: continuous release, controlled release, delayed release, depot, gradual release, long term release, programmed release, prolonged release, programmed release, proportionate release, protracted release, repository, retard, slow release, spaced release, sustained release, time coat, time release, delayed action, extended action, layered time action, long acting, prolonged action, sustained action medications and extended release, release in terms of pH level in the gut and intestine, breakdown of the molecule and based on the absorption and bioavailability.

Hydrogels, wherein compositions of the present invention are dissolved in an aqueous constituent to gradually release over time, can be prepared by copolymerization of hydrophilic mono-olefinic monomers such as ethylene glycol methacrylate. Matrix devices, wherein compositions of the present invention are dispersed in a matrix of carrier material, can be used. The carrier can be porous, non-porous, solid, semi-solid, permeable or impermeable. Alternatively, a device comprising a central reservoir of compositions of the present invention surrounded by a rate controlling membrane can be used to control the release of the compositions. Rate controlling membranes include ethylene-vinyl acetate copolymer or butylene terephthalate/polytetramethylene ether terephthalate. Use of silicon rubber depots are also contemplated.

Controlled release oral formulations are also well known. In one embodiment, the compositions of the present invention are incorporated into a soluble or erodible matrix, such as a pill or a lozenge. In another example, the oral formulations can be a liquid used for sublingual administration. These liquid compositions can also be in the form of a gel or a paste. Hydrophilic gums, such as hydroxymethylcellulose, are commonly used. A lubricating agent such as magnesium stearate, stearic acid, or calcium stearate can be used to aid in the tableting process. In a preferred embodiment, transdermal patches, steady state reservoirs sandwiched between an impervious backing and a membrane face, and transdermal formulations, can also be used to deliver compositions of the present invention. Transdermal administration systems are well known in the art. One type of transdermal patch is a polymer matrix in which the compositions of the present invention are dissolved in a polymer matrix through which the compositions of the present invention diffuse to the skin.

The transitional phrase "consisting essentially of" limits the scope of a claim to the specified materials or steps and those that do not materially affect the basic and novel characteristics of the claimed invention. Thus, for example, a composition consisting essentially of an inositol-stabilized arginine silicate complex and free inositol would not include other ingredients that are known to treat and/or prevent cognitive decline, or improve cognitive function.

The compositions of the present invention may be administered once, twice, or three times per day. In some embodiments, the compositions of the present invention are administered four times a day. For example, the compositions of the present invention may be administered before, after, or during a meal. In some embodiments, the compositions of the present invention may be administered before performing an activity requiring cognitive function. For example, the compositions of the present invention may be administered before playing a video game, before operating an unmanned vehicle, before participating in a sport that requires physical and cognitive functioning, such as football, soccer, rugby, lacrosse, basketball, hockey and the like.

While the present invention has been described in some detail for purposes of clarity and understanding, one will appreciate that various changes in form and detail can be made without departing from the true scope of the invention.

EXAMPLES

The compositions comprising ASI (Nitrosigine®—1,500 mg/day) and free inositol (100 mg/day) "ASI+I" were tested in a randomized, double-blind, placebo-controlled, parallel group, prospective clinical trial using the Trail Making Test B (TMT) and the Stroop Test as the cognitive outcomes measure. TMT B involves connecting an alternating sequence of numbers and letters. TMT B evaluates visual search, speed of processing, mental flexibility, and executive functions under pressure. The Stroop Test detects whether there is a conflict or interference between brain pathways processing specific types of information. The Stroop Test requires subjects to name the 'ink color' of a 'color word'. The color word is either the 'same as' (congruent with) or 'not the same as' (incongruent with) the ink color. The Stroop Test evaluates the selective attention that requires interference resolution, response inhibition, response selection, and reaction time. The study described in the following examples was conducted to determine if the benefits of ASI+I transfer to video game players that need a strong cognitive state and may benefit from a nutritional supplement that can improve concentration, decrease reaction time, and increase energy levels. In this study, the composition used contained ASI and includes additional inositol "ASI+I".

Example 1

A total of 60 healthy male and female adult subjects, aged 18 to 40 years old inclusive, with a body mass index (BMI)

of 18.0 to 34.9 kg/m² inclusive, who on average spend 5 or more hours a week playing video games for 6 months prior were randomly assigned in a 1:1 ratio to receive either ASI+I or placebo. The randomization was stratified by BMI of 18.0 to 27.0 and 27.1 to 34.9.

TMT B and Stroop Test were conducted pre-dose, at least 15 minutes post-dose, and following 60 minutes (+/−5 minutes) of video game playing on day 1 and day 7.

ASI+I was taken once daily and contained 1500 mg ASI+100 mg of additional inositol as active ingredients, and also contained citric acid, natural flavor, sucralose, acesulfame potassium, and red 40 as inactive ingredients.

Placebo was taken once daily and contained 0 mg ASI+0 mg of additional inositol, and also contained maltodextrin, citric acid, natural flavor, sucralose, acesulfame potassium, and red 40.

On day 1, subjects were randomly assigned to the placebo or ASI+I group, and TMT B and Stroop Test were conducted pre-dose, at least 15 minutes post-dose, and following 60 minutes (±5 minutes) of video game playing.

Subjects were instructed to take the product (either placebo or ASI+I) once daily and to continue with normal routine regarding video game play.

On day 7, subjects conducted TMT B and Stroop Test pre-dose, at least 15 minutes post-dose, and following 60 minutes (±5 minutes) of video game playing. Day 7 was the last dose of the product.

Total time for conducting the TMT B and Stroop Tests, as well as the number of errors committed during each test were recorded for all the time points.

As shown in FIG. 1, the number of errors committed in the TMT B significantly decreased 15 minutes post-administration of ASI+I compared to placebo.

Figure 2:
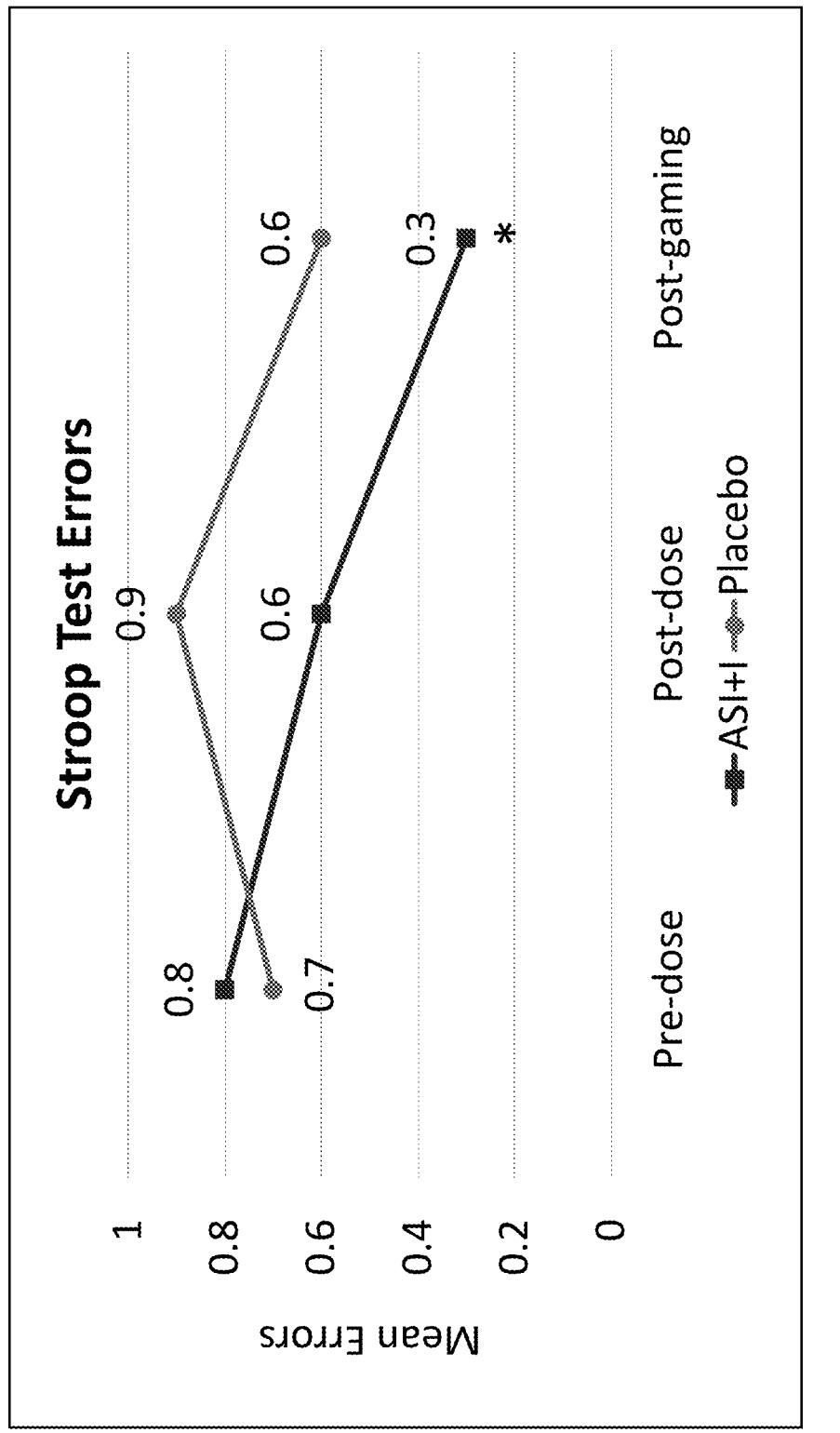
FIG. 2 is a line graph summarizing the results of average number of errors committed by subjects in the Stroop test. Subjects received either placebo or a composition comprising ASI (1,500 mg) and free inositol (100 mg). The Stroop test was performed prior to treatment (baseline), 15 minutes post-administration of the composition and post-video game play of 60 minutes.

As shown in FIG. 2, the number of errors committed in the Stroop Test decreased 15 minutes post-administration of ASI+I compared to placebo and post-gaming.

This is unexpected given prior studies conducted with just ASI, which demonstrated that subjects taking ASI committed more errors in the TMT B test compared to placebo 15 minutes post-administration of product (see Table 1 below).

TABLE 1

| | TMT B Errors (±SD) | |
|---|---|---|
| | Pre-Dose | Post-Dose |
| ASI | 0.5 ± 0.1 | 0.3 ± 0.5 |
| Placebo | 0.8 ± 0.9 | 0 ± 0 |

What is claimed is:

1. A method of improving cognitive functioning in a human comprising:
administering an amount of an inositol-stabilized arginine silicate complex and free inositol effective to improve cognitive functioning in the human.

2. The method of claim 1, wherein the amount of inositol-stabilized arginine silicate complex administered is between about 0.5 g to 5 g per day.

3. The method of claim 1, wherein the amount of inositol-stabilized arginine silicate complex administered is about 1,500 mg per day.

4. The method of claim 1, wherein the amount of free inositol administered is between about 0.01 g to 1 g per day.

5. The method of claim 1, wherein the amount of free inositol administered is about 100 mg per day.

6. The method of claim 1, wherein the improving cognitive functioning comprises improving visual construction in the human, improving executive function in the human, improving visual search in the human, improving motor speed skills in the human, improving mental flexibility in the human, improving selective attention in the human, improving interference resolution in the human, improving response inhibition in the human, improving response selection in the human, and/or improving reaction time the human.

7. The method of claim 1, wherein the improving cognitive functioning comprises increasing the speed to perform a task, decreasing the number of errors when performing a task, improving performance when playing a video game, and/or more accurate control of an unmanned vehicle or remote controlled vehicle.

8. The method of claim 7, wherein, improving performance when playing a video game comprises increasing a high score in a video game, playing the game at a more difficult level/setting, scoring more points/goals in a sports simulation video game, hitting more targets in a shooter video game, beating more opponents in a multiplayer video game, and/or hitting an opponent more times in a fight simulation video game.

9. The method of claim 7, wherein more accurate control of an unmanned vehicle comprises decreasing the number errors while controlling the unmanned vehicle, and/or increasing the number of targets acquired by the unmanned vehicle.

10. The method of claim 7, wherein more accurate control of a remote controlled vehicle comprises decreasing the number errors while controlling the remote controlled vehicle.

* * * * *